(12) United States Patent
Pappas

(10) Patent No.: US 7,151,372 B2
(45) Date of Patent: Dec. 19, 2006

(54) METHOD AND MEANS OF MULTI-ACTIVATION OF IONS AND ATOMS WITH NMR AND EPR

(76) Inventor: Panagiotis T. Pappas, 26 Markopoulioti Street, Athens (GR) GR-11744

( * ) Notice: Subject to any disclaimer, the term of this patent is extended or adjusted under 35 U.S.C. 154(b) by 0 days.

(21) Appl. No.: 10/550,375

(22) PCT Filed: Jun. 29, 2004

(86) PCT No.: PCT/GR2004/000037

§ 371 (c)(1),
(2), (4) Date: Sep. 19, 2005

(87) PCT Pub. No.: WO2005/001496

PCT Pub. Date: Jan. 6, 2005

(65) Prior Publication Data

US 2006/0220648 A1    Oct. 5, 2006

(30) Foreign Application Priority Data

Jun. 30, 2003   (GR) .............................. 20030100282

(51) Int. Cl.
*G01V 3/00*   (2006.01)
(52) U.S. Cl. ...................... 324/318; 324/322
(58) Field of Classification Search ............... 324/318, 324/322, 319, 309, 307, 300, 306, 312, 314; 600/410–422
See application file for complete search history.

(56) References Cited

U.S. PATENT DOCUMENTS

| | | | |
|---|---|---|---|
| 3,083,335 A * | 3/1963 | Schuster ..................... 324/303 |
| 4,710,713 A | 12/1987 | Taicher | |
| 5,296,811 A | 3/1994 | Ehnholm | |
| 5,432,446 A | 7/1995 | MacInnis | |
| 5,488,342 A | 1/1996 | Hanley | |
| 5,677,630 A | 10/1997 | Laskaris | |
| 5,712,566 A * | 1/1998 | Taicher et al. .............. 324/303 |
| 5,835,995 A * | 11/1998 | Macovski et al. .......... 324/309 |
| 5,936,404 A | 8/1999 | Ladebeck | |

FOREIGN PATENT DOCUMENTS

| | | |
|---|---|---|
| EP | 0 823 639 A | 2/1998 |
| WO | WO 97/13159 A | 4/1997 |
| WO | WO 02/056047 A | 7/2002 |

\* cited by examiner

*Primary Examiner*—Brij B. Shrivastav
(74) *Attorney, Agent, or Firm*—Myers Dawes Andras & Sherman LLP; Vic Lin; Joseph Andras

(57) ABSTRACT

The invention uses one inductor, which is formed of one, two or a few twisted or parallel conductors, and exposes a sample object in a pulsed and damped alternating magnetic field (B) without necessarily the employment of a second, constant intensity, magnetic field. In this way, the nuclei and/or the electrons of the sample object are activated, in the presence of a non-constant magnetic field (B), that gets infinite negative and positive values between successive damped positive and negative values, crossing through the zero value during a magnetic pulse. Thus, a wide nuclear NMR and electronic EPR multiple—resonance of the sample object is achieved.

14 Claims, 8 Drawing Sheets

METHOD AND MEANS OF MULTI-ACTIVATION OF IONS AND ATOMS WITH NMR AND EPR

Figure 1:
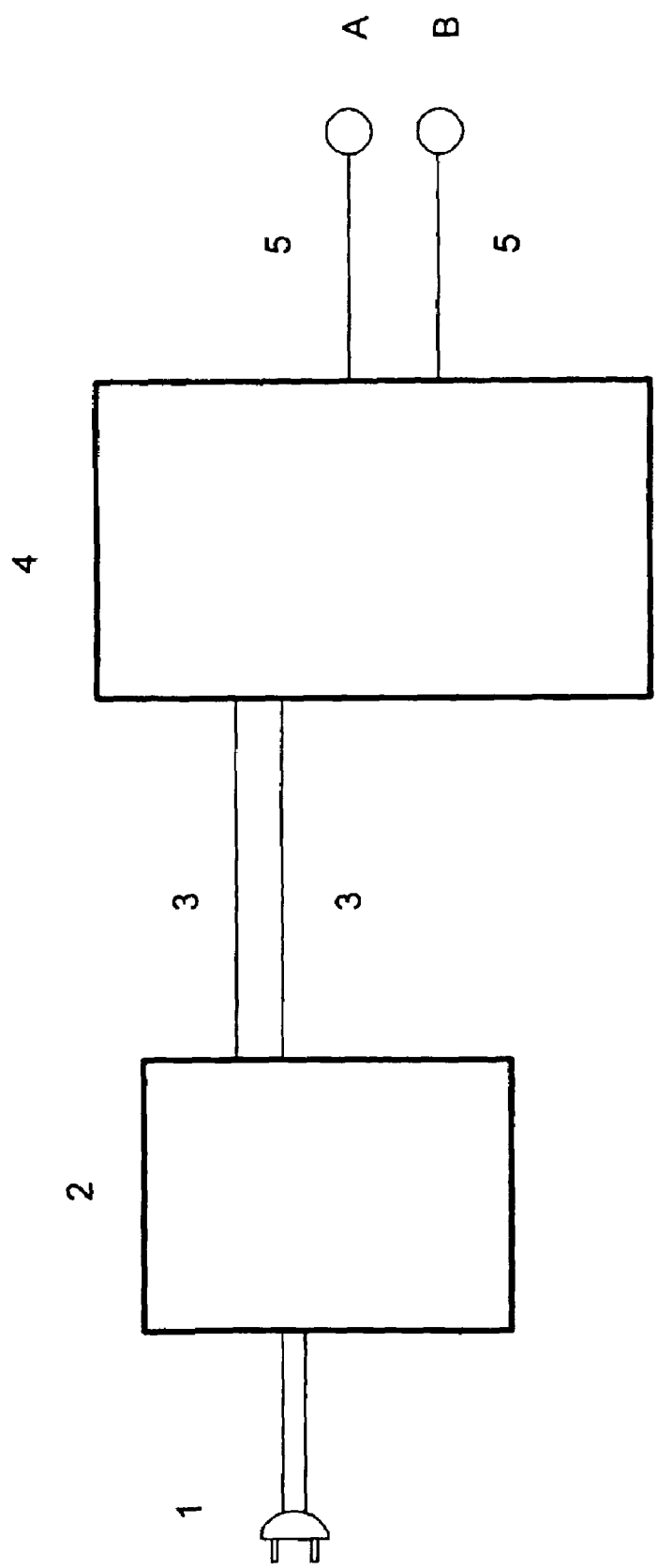

The method of Nuclear Magnetic Resonance (NMR) for the Atomic Nucleus and of the Electron Paramagnetic Resonance (EPR) for the Atomic Electrons respectively, consists in the use of two geometrically vertical magnetic fields. The intensity of one of them is kept constant, and is usually in the order of 2 Tesla, as in NMR Imaging.

The intensity of the second magnetic field is pulsed and its aim is to divert the already oriented on the constant magnetic field atomic nuclei (or electrons), which returning to their previous state emit the absorbed energy in the form of radiated electromagnetic energy. The frequency of the said electromagnetic energy depend on the intensity B of the applied constant magnetic field, $\Delta E = h\nu = \gamma Bh/2\pi$, from the acoustic frequencies band, up to the microwaves band, cf. W. Atkins Physical Chemistry Book, Oxford University Press, 1994, Fifth Edition, p. 625.

Two main applications of Nuclear Magnetic Resonance are NMR spectroscopy and Magnetic Representation (Nuclear Magnetic Resonance Imaging NMRI or more widely known as MRI) otherwise known in Medicine as Magnetic Diagnostic Tomography. With the technique of Nuclear Magnetic Resonance, a sample is placed in a constant intensity B magnetic field and is exposed to the pulses of a second magnetic field. After the pulse emission pause, the response echo is recorded from the sample and analyzed. Bibliography: Nuclear Physics K. Alexopoulos, Athens 1967, Magnetism in Medicine, edited by Andra and Nowak, Wiley 1998, Scientific American, February 1968.

The Phenomenon of Gyroscopic Precession.

The phenomenon of gyroscopic precession for gyroscope is caused by an off-centre force, which, nevertheless, does not accomplish a complete re-orientation. In order for the gyroscope to maintain the general orientation in space, it follows a precession around the axis of its initial orientation. Thus, on an average, the gyroscope maintains the original direction of its rotation axis. This phenomenon is named "the natural precession of the gyroscope".

Generally, the electrons and the protons are gyroscopes that is they possess angular momentum J and magnetic momentum, M, spin, namely, they are magnets.

They can be considered annular gyroscopes (circular orbits) of closed electrical currents, loops, which possess angular momentum J and magnetic momentum M. They also possess charge $q=+/-e$ and mass, m, that is to say they are characterized by m, q, J, M and can be considered as Electric and Magnetic rotating Gyroscopes.

The Frequency of Precession of a gyro is usually much-much smaller than the frequency of their rotation. This also applies to the frequency of precession of protons-electrons.

When the Protons and the electrons precess, as described above, they can emit radio waves of relatively low frequency, and can return to their original (spin), without precession. These radio waves are the basis of magnetic resonance that come from NMR and EPR and that (NMR) is the basis of NMRI, which is used in medicine for diagnostic purposes. Obviously, the protons—electrons rotating magnetic gyroscopes—are very easily disturbed and can begin to undergo a precession, after the sudden presence of a magnetic field or a magnetic pulse, in the presence of another restoring magnetic field. This observation is the basis of the present invention described below:

The first fundamental objective of the present invention is the NMR and EPR multi-resonance. To achieve this aim it employs only one inductor (coil) which is comprised of a coil of one, two or few turns of twisted or parallel conductors instead of the two magnetic fields of the known methods NMR and EPR, thus exposing the sample to a pulsed and damped-wave alternating magnetic field B without the use of a second constant intensity B magnetic field. Thus activating the nuclei and the electrons of a sample object, in the presence of the magnetic-field of the Earth and in the presence of a non-constant magnetic field B that repeats infinite negative and positive values between a maximum positive absolute value and zero intensity during each magnetic pulse (around 10 to 50 microseconds).

In this way, a wide nuclear NMR and electronic EPR multiple-resonance of the sample is achieved, according to the law: $\Delta E = h\nu = \gamma Bh/2\pi$, see W. Atkins Physical Chemistry Book, Oxford University Press, 1994, Fifth Edition, p. 625, with B variable were B is the resultant of the magnetic field of the Earth field and of the damping oscillation of the applied coil.

The effect of magnetic pulses on biological matter, outside and around the cells of organisms, is generally known in the medical world. The present method as well as the previous invention 1001784/6/21995/OBI of the inventor are able to effect NMR, EPR and to induce electric charges, ion concentrations or concrete atoms, inside organic or inorganic matter, inside biological matter, or inside any kind of matter in which exist movable electric charges or atoms, for which however an exceptionally high impetus is required in order to overcome the high potential barrier existing on both sides of the cellular membrane.

As it was reported above, the present invention can also cause multi-NMR and EPR.

The present method employs a device that in the presence of the ambient magnetic field of the Earth or not, produces a damped magnetic field with the help of discharges via any electronic arrangement of conductivity switches, either electronic, or an otherwise equivalent switch arrangement, for example a plasma discharge, that can be suitably activated by any "external" means, i.e. any sort of trigger arrangement or by self-activated avalanche effect.

The exposed method and device produce a damped magnetic field that possess the characteristics of maximum instantaneous power and very small temporal duration which result from an electric arrangement of a large capacity and, at the same time, of small self-induction and almost zero output load.

The use of damped alternating magnetic fields also causes induced electrical tension in a single surface loop or volume (induction in a one turn coil), at most equal in the order of magnitude to the initial electrical tension of the source that alters the magnetic flow.

In order to achieve the above described results from a distance, which will be comparable with the above magnitudes and to be practically feasible, the present method employs arrangements of switches, that can be of any type from the known types of semiconductors, or plasma discharge switches, as the plasma oscillations which had been employed for this purpose and which have been observed in electrical discharges through various gases, as it has been reported with the previous invention.

This new method is also ideal for the supply of electric currents in medicine by induction, where electric circuits can be formed between cellular regions, without the need for the inevitable invasion or for some form of surgery in order to achieve electrode contact. It is also suitable for the activation of the atomic nuclei because of the phenomenon of Nuclear Magnetic Resonance NMR and respectively for the electrons of atoms because of the phenomenon of Electron Paramagnetic Resonance EPR, that can lead to Biological Nuclear transmutations, see Louis Kervran Biological Transmutations ©1972 Swan House Publishing Co.

The method is applied without the need for physical contact, even over clothes and it can penetrate in-depth proportional with the intensity level employed, because it is known that the magnetic field can effectively act from a distance and particularly through biological tissue.

It has also been observed that the magnetic field can achieve catalysis of chemical reactions, see bibliographic reports:

M. YAOITA, T. WADA et al., Electrochemical study of enzymatic reaction of glucose oxidase in magnetic fields Abstract: 17th ann Mtg. BEMS, Boston, Mass., June 1995.

W. HABERDITZL Enzyme activity in High magnetic fields. Nature 7 Jan. 1967, p73 (1967).

A.S.M. I. NAZAR, a PAUL et al., Frequency dependent alteration of enolase activity by electric, magnetic and combined EM ELF Fields Abstract: 17th Annual Mtg. BEMS Boston Mass., June 1995.

S. COMOROSAN, S. VIERU & P. MURGOCI The effect of electromagnetic field on enzymic substrates. Biochim. Biophys. Acta. 268,620–621.1972).

E. S. COOK & M. J. SMITH Increase in Trypsin activity in Biological Effects of magnetic fields, pp 246–254, Plenum Press, NY, 1964

The present method has various other applications without the need for direct electrical contact, whenever the activation of specific atoms, nuclei, ions or charges, formation of selected chemical compounds, nuclear transmutations, (e.g. according to Kervran) are required.

That is, we have the promotion of a catalytic action or activation (nuclear) from a distance that maintains, accelerates or initiates a potential chemical or nuclear reaction that otherwise would not happen or would proceed with a very slow rhythm.

An embodiment of the method becomes apparent from the following sample of the so called PAPIMI device. (PAPIMI stands for Pappas Ion Magnetic Induction) device that is pictured in FIGS. 1, 2a, 2b, 3a, 3b, 4a, 4b, 5. The PAPIMI device operates in the ambient magnetic field of the Earth with its induction coil held (21), (21a) held preferably with its axis perpendicular to the ambient magnetic field (of the Earth), and consists of a power supply cord (1) FIG. 1, that provides electrical energy 230 Volts, 50/60 Hz to the control unit (2) FIG. 1, a switch, timer switch and a switch regulated output transformer of 30 Kilovolts, from a unit (4) FIG. 1 which is connected via high electrical tension lines (3) FIG. 1 with the high tension transformer's output of the unit (2) FIG. 1. The unit (4) FIG. 1 rectifies the transformer's high tension. The high tension charges via the high tension lines (5) FIG. 1 and contacts A and B energy reservoir (7), FIGS. 2a, 2b which is a 0.05 μF capacitor and 50 Joules energy storage capacity and has a great speed of discharge, which results in very high power discharge in the order of GigaWatts. The energy reservoir is connected to the high tension and high current carrying capacity line (6A) FIGS. 2a, 2b with, either the electronic switch arrangement (14) FIG. 2a, or with any other equivalent switch, i.e. plasma discharge switch (14) FIG. 2b.

Figure 2A:
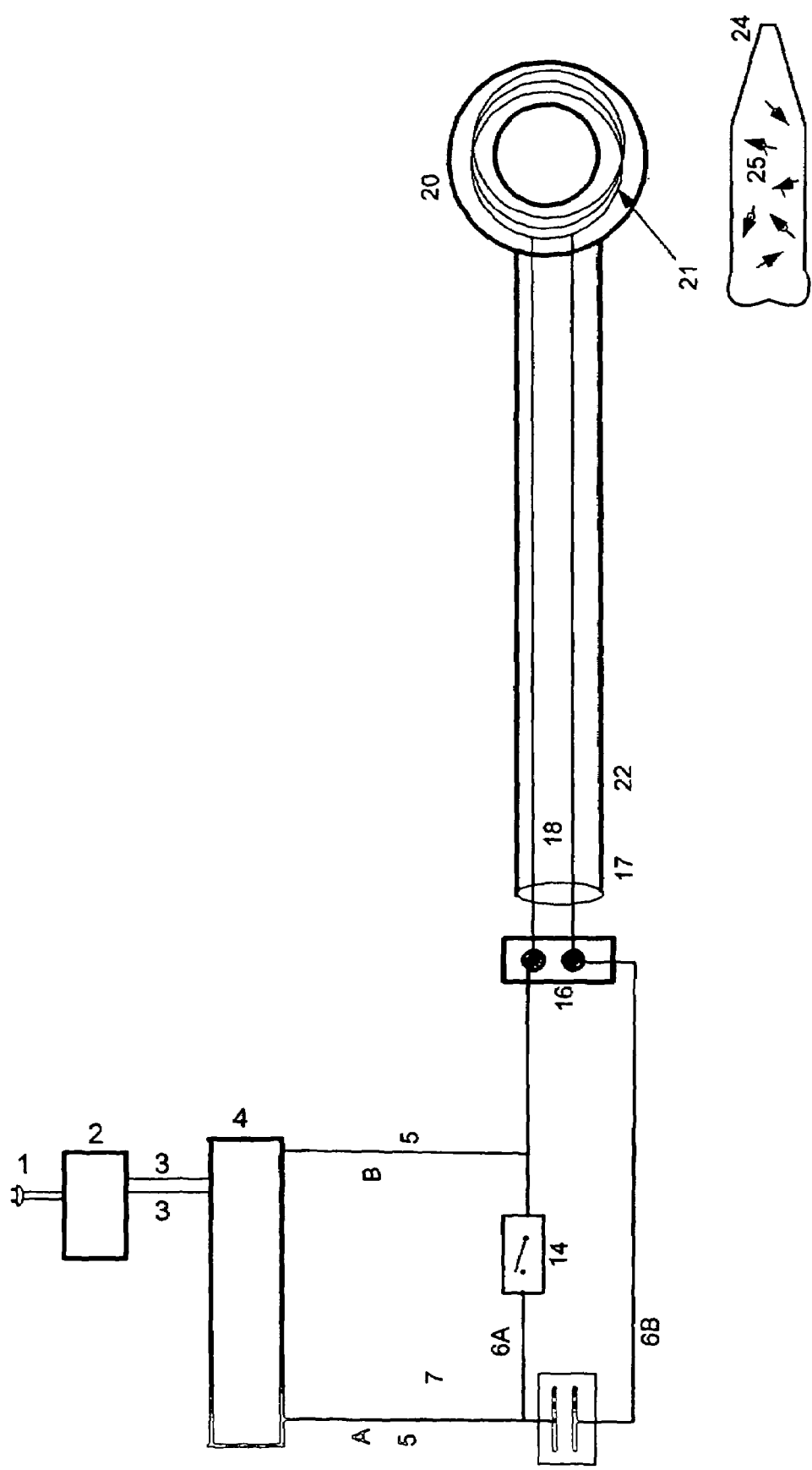
Figure 2B:
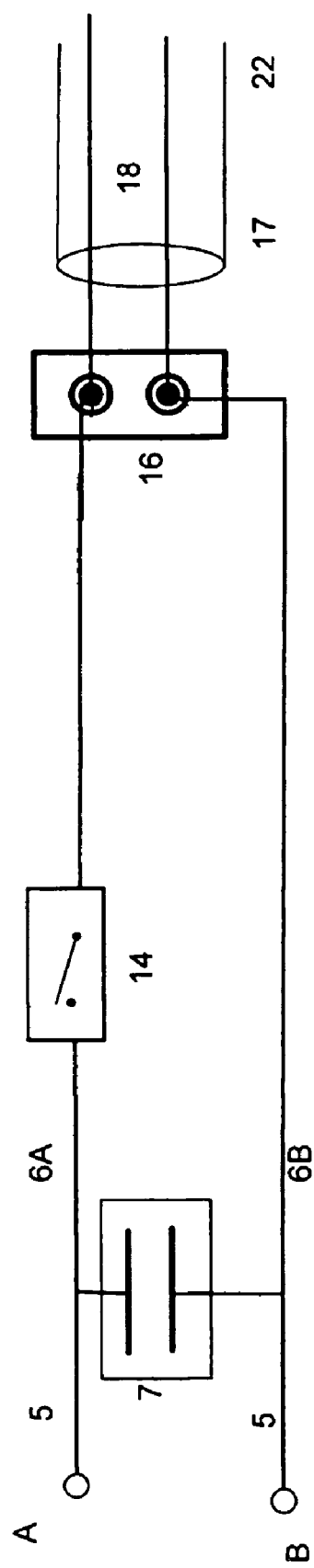

Specifically, this switch arrangement (14) FIGS. 2a, 2b, is constituted of a suitable electronic arrangement either of:
a) One or more semi conductive elements switch, (14) which are connected with one of the two leads of the connection box (16) FIG. 2a.

One terminal of the connections box (16) FIG. 2a is connected with the one terminal of the energy reservoir (7) FIG. 2a, via the high current and intensity line (6B) FIG. 2a.

Line 6A connects the other terminal of the energy reservoir (7) FIG. 2a with the other end of said semi conductive elements (14) switch to the capacitive energy storage bank.

Capacitive energy storage bank is connected via leads (5) through connection points (A) and (B) with the high-tension power supply unit.

Figure 3A:
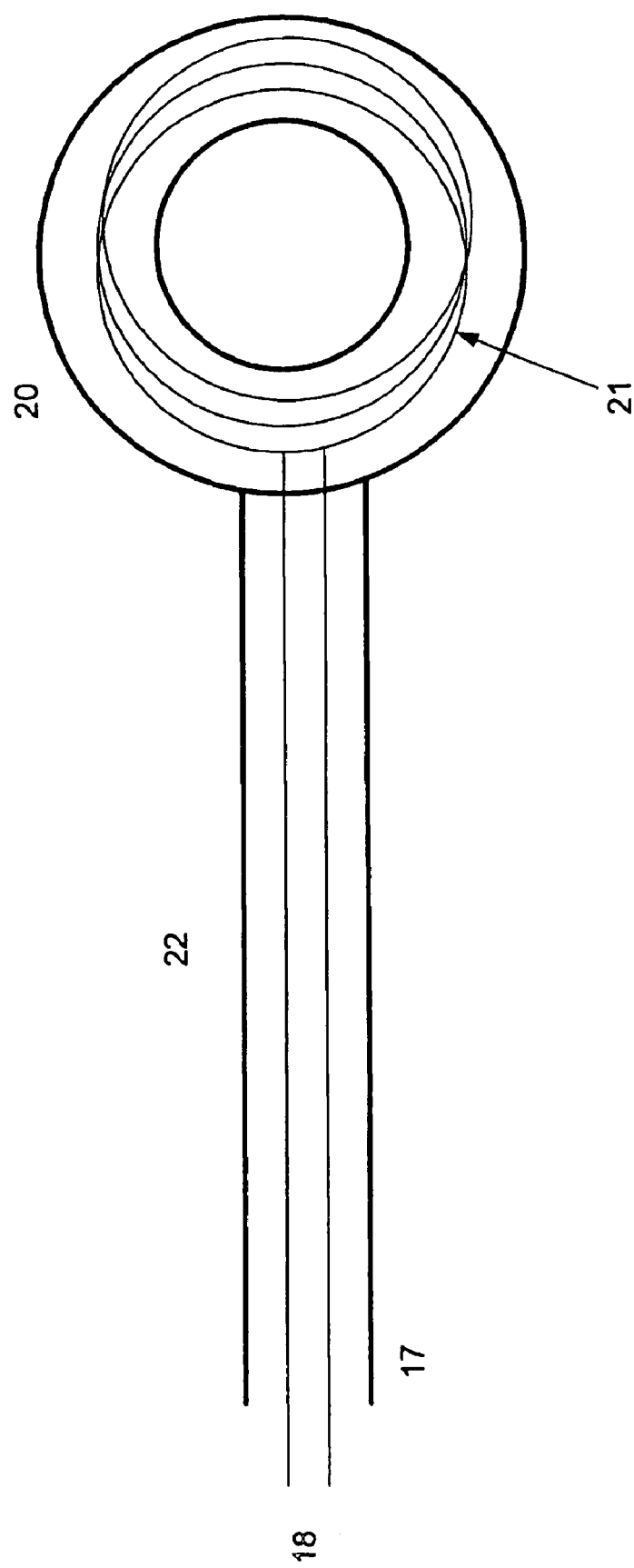
Figure 3B:
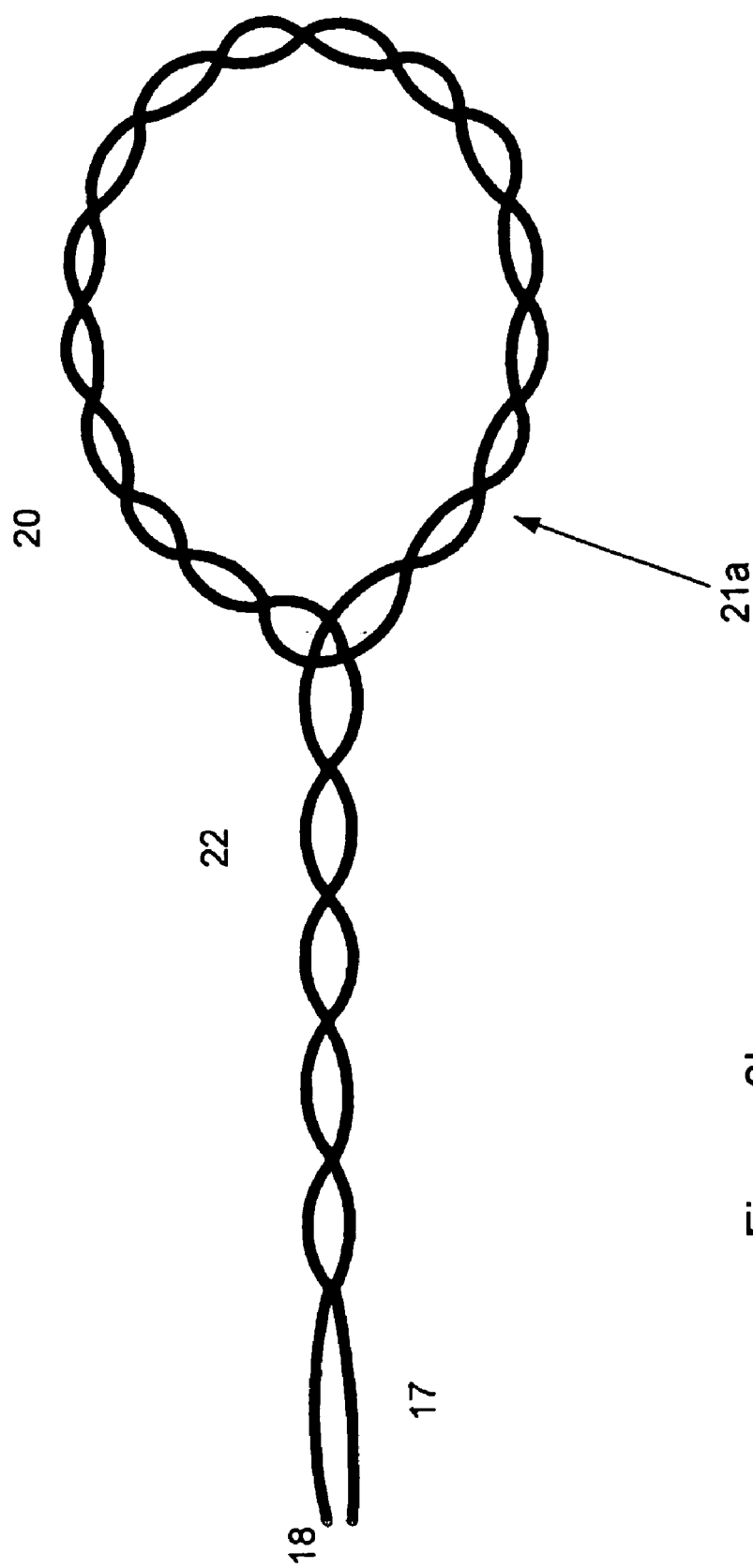

Inductor (22) FIGS. 2a, 3a, 3b is connected to the connection box (16).

Or b) Any other equivalent switch i.e. a plasma discharge switch, (14) which is connected to the energy reservoir (7) FIG. 2b via Line 6A and also with the one of the two leads of the connection box (16) FIG. 2b.

The other lead of the connection box (16) FIG. 2b is connected to the other terminal of the energy reservoir (7) FIG. 2b via the high tension and high current carrying capacity flexible line (6B) FIG. 2b.

Said plasma discharge switch, (14) is connected via leads (5) through connection points (A) and (B) with the high-tension power supply unit.

Similarly, inductor (22) FIGS. 2a, 3a, 3b is connected to the connection box (16).

The inductor (22), FIGS. 3a, 3b, 4a, 4b, consists of the transport line (18) with specifications for very high power, very high electrical tension and very high current carrying capacity, and is surrounded by a cylindrical, high tension withstanding insulation (17) FIGS. 3a, 3b, 4a, 4b. Finally, the inductor's transport line (18) FIGS. 3a, 3b, 4a, 4b connects the inductive coil which is comprised of one, two or few twisted (21a) FIG. 3b, or parallel conductors (21) FIG. 3a, that is placed inside the ring's (20) FIGS. 3a, 3b high-tension insulation. The cylindrical insulation (17) FIGS. 3a, 3b, 4a, 4b and the overall ring constitute a waterproof concave body, as they are portrayed in FIGS. 3a, 3b, 4a and 4b, in order to provide proper insulation and protection for the objects they surround, without blocking the exit of magnetic lines (23) FIGS. 4a, 4b from the ring (20) FIGS. 3a, 3b, 4a, 4b. Under the ring (20), exhibit (24) is placed at a distance preferably no greater than the ring's diameter.

The invention operates as follows: After the energy's reservoir capacitor (7) FIGS. 2a, 2b electrical tension is increased beyond a critical value, then either the electronic switch arrangement (14) FIG. 2a, or any other equivalent switch e.g. a plasma switch (14) FIG. 2b is fired, that can by suitable activation or by self-activation of the avalanche effect, thus becoming conductive, which results in the creation of a damped wave oscillating electrical current.

Figure 4A:
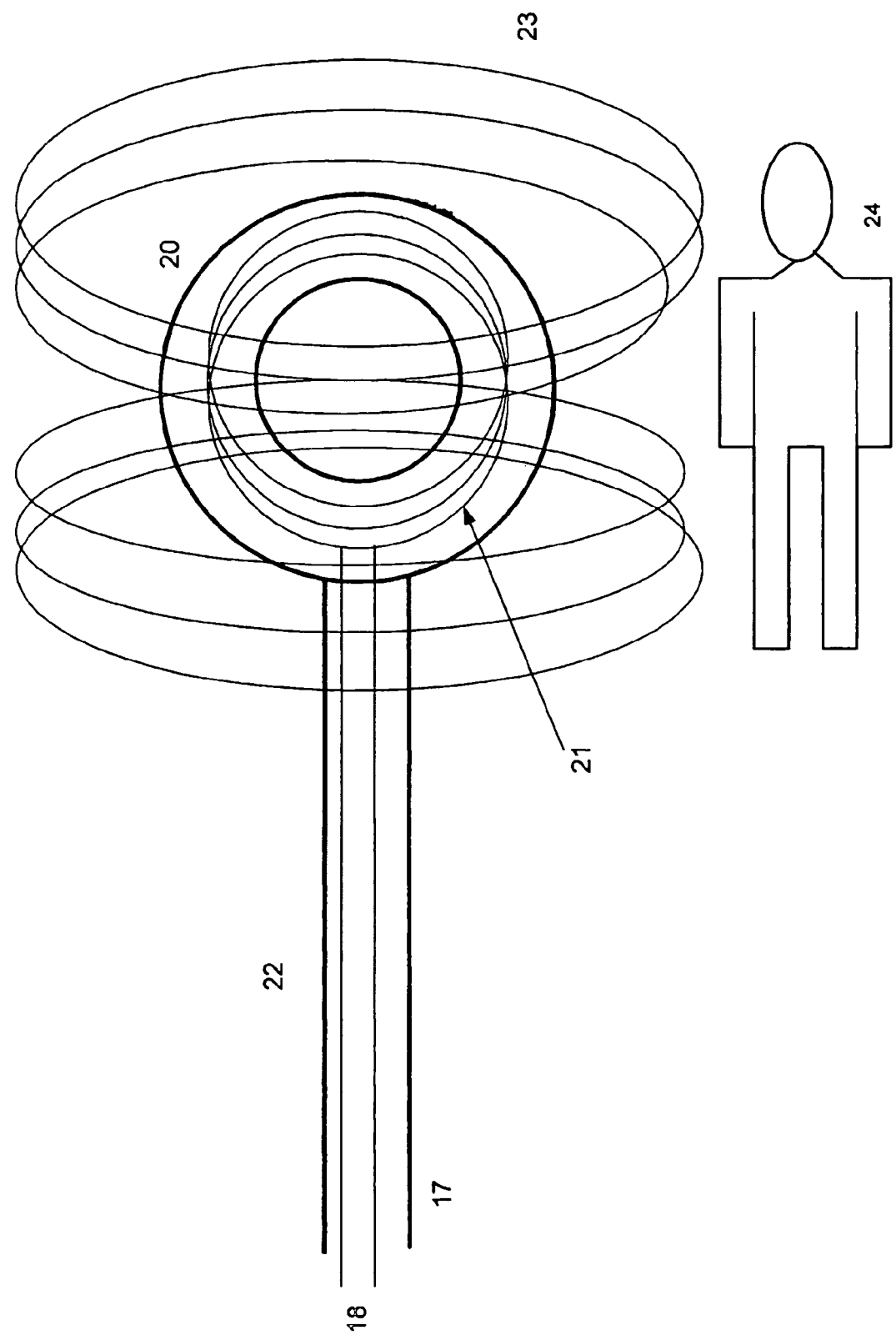
Figure 4B:
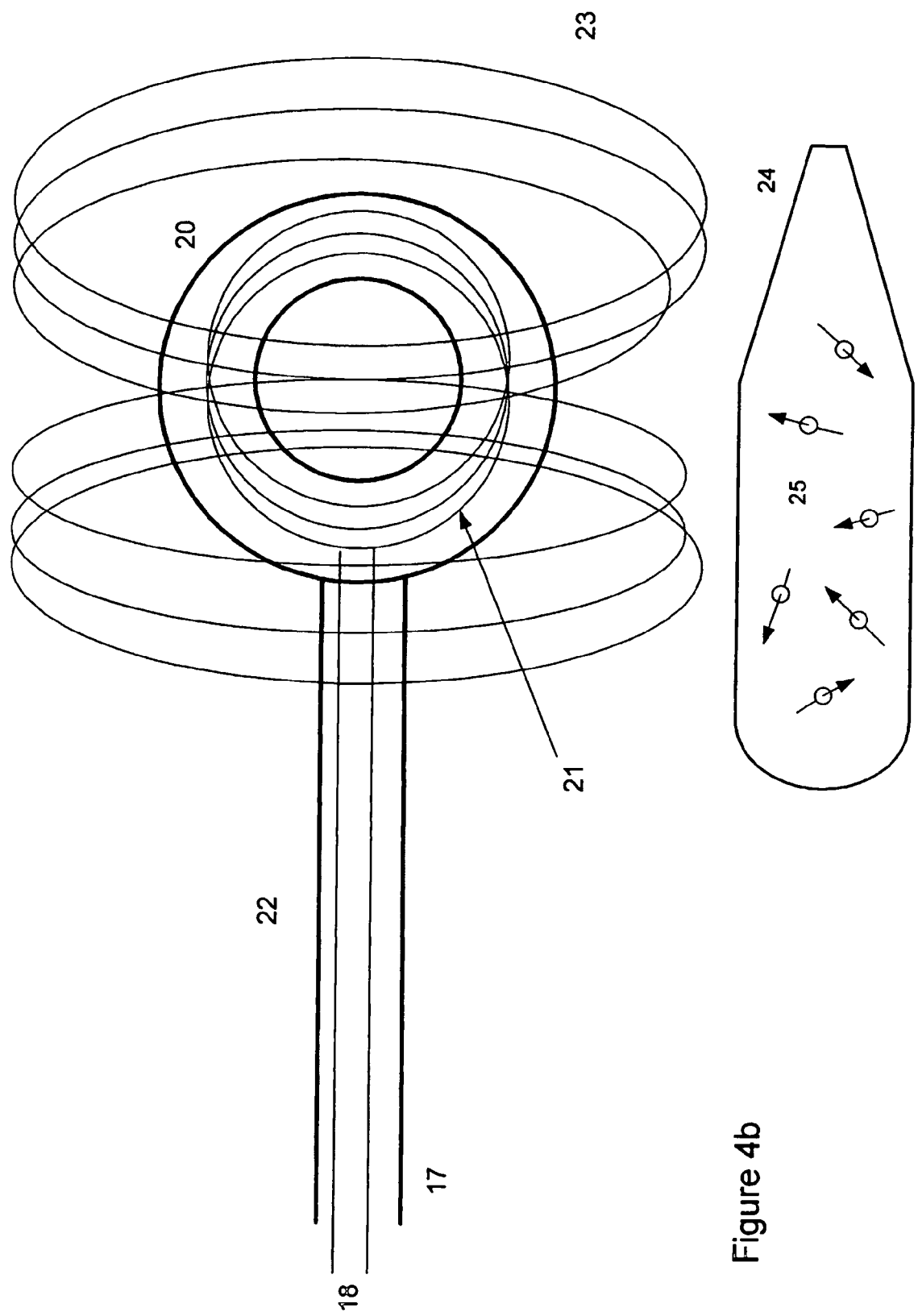
Figure 5:
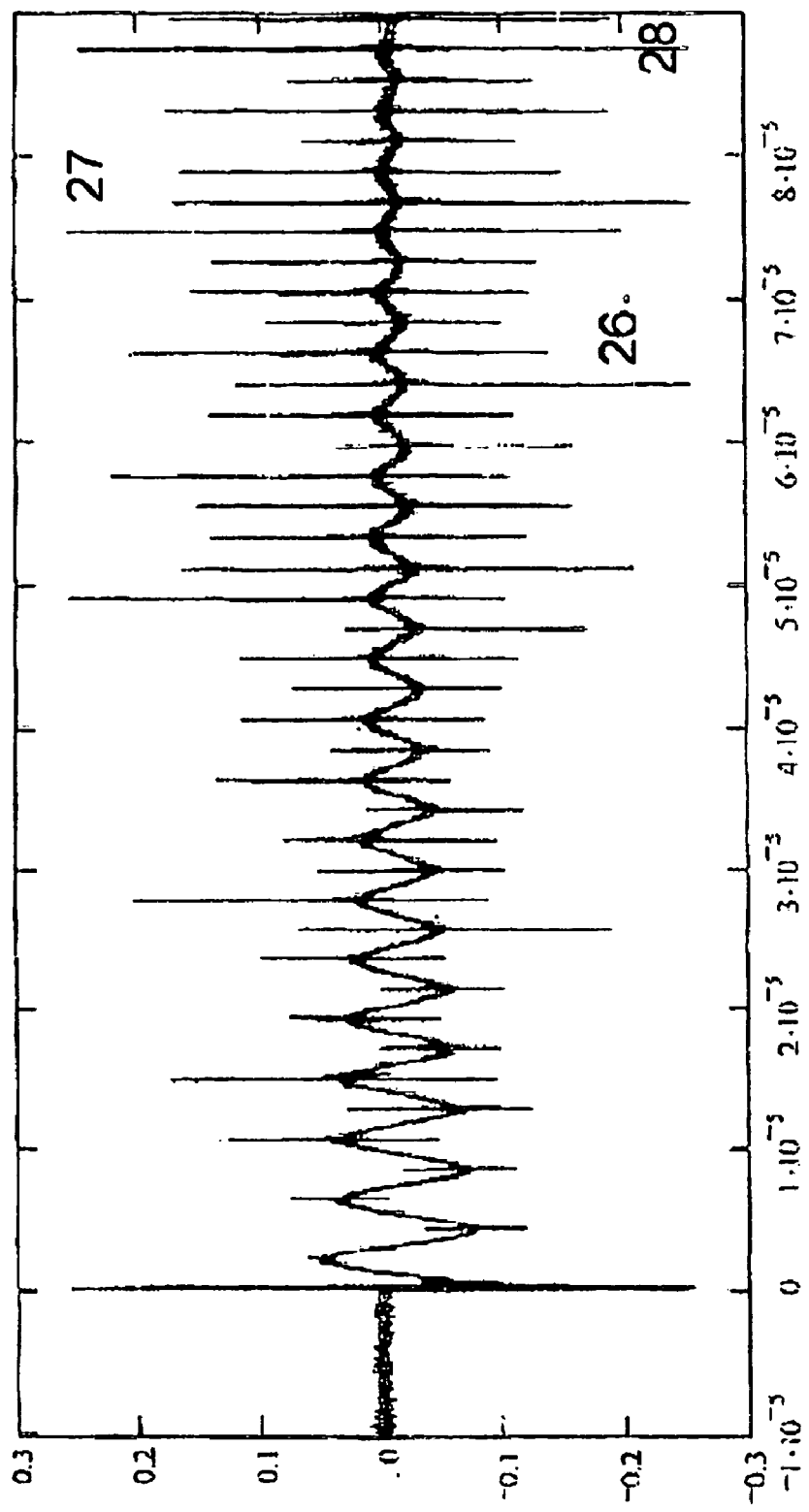

The damped and oscillating electric current, as portrayed in the oscillogram of FIG. 5 in the electronic switch arrangement (14) FIG. 2a or in any other equivalent switch i.e. plasma discharge switch (14) FIG. 2b, is channeled to the inductor (21) FIGS. 3a, 3b. The inductor (21) which is comprised of one, two or few coil turns of twisted (21a) or parallel (21) conductors FIGS. 3a, 3b 4a, 4b produces a similarly altered with the electric current oscillations magnetic field flow.

After the discharge of the last pulse from the unit (4) FIG. 1, after the firing of the electronic switch (14) FIG. 2a or any other equivalent switch e.g. a plasma discharge switch (14) FIG. 2b, and after the first pause, the reservoir-capacitor (7) FIGS. 2a, 2b is practically empty. During the pulsations pause of the unit (4) and without any available electric power, the conductivity of the switch is suspended.

Arrangement (14) FIGSA. 2a, 2b becomes once again non-conductive, giving opportunity for the reservoir (7) FIGS. 2a, 2b to be recharged again by the unit (4) to the highest critical electrical tension and then for a new conductivity firing to occur. The cycle is then repeated, in the same way as before.

Under inductor coil which is consisted of one, two or few twisted (21a) FIG. 3b or parallel (21) FIG. 3a conductors the similarly altered magnetic flow (23) FIGS. 4a, 4b intercepts exhibit (24) FIGS. 4a, 4b. In the presence of an ambient magnetic field or not, nuclear and electronic spins (25) are reoriented in exhibit (24) and they are causing multi-NMR and EPR, (26), (27), (28) FIG. 5 (because of the variability of the magnetic field intensity B), ions are induced and, electrical charges are moved in general. Elements whose resonant frequency coincides with the frequency that corresponds to the formula $hv = \gamma Bh/2\pi$, or to the induced current frequency, absorb the highest amount of energy.

The damped wave form of energy of this method, allows the instantaneous power of these oscillations to be much greater than the average power. Also, the NMR echo signals are delayed, a short time after the main damped wave oscillating pulse "hits" the sample (26), (27), (28), FIG. 5.

Thermal effects (which are proportional to the average power of the oscillations) are limited, while phenomena that depend on impactive (immediate) value of electrical tension are increased, i.e. NMR and EPR are enhanced (26), (27), (28), FIG. 5, or the rendering of chemical reactions is increased, which when they are exposed to the device's magnetic induction in order to take place, require an electrical "push" above a high critical value. A specific example of this is the movement of electric charges through the cellular membrane.

Another example of NMR is the activation of sodium Na and oxygen O nucleus, so as to allow the thermonuclear reaction Kervran-Pappas to take place:

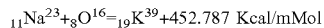

$_{11}Na^{23} + _8O^{16} = _{19}K^{39} + 452.787$ Kcal/mMol

That is, the activation of nuclei takes place, and consequently so do nuclear reactions via Nuclear Magnetic Resonance.

In this way, by selecting a suitable electrical characteristic switches arrangement (14), FIGS. 2a or 2b, a suitable self induction L around 1 µH for the inductor), which is comprised of one, two or few twisted (21a) FIG. 3b or parallel (21) FIG. 3a conductors a sufficiently high electrical tension for the power supply and a suitable frequency for the pulses produced by the unit (4) FIG. 1, an inductive oscillating tension in the exhibit (24) FIGS. 4a, 4b, can be achieved, which is characterized by a specific resonant frequency, or resonant frequencies spectrum.

Due to the fact that there is not enough time between two cycles of operation, for the activated nuclei to get deactivated, the quantity of exhibit's (24) FIGS. 4a, 4b activated nuclei (25) and/or electrons (25) FIGS. 4a, 4b and (26), (27), (28), FIG. 5 increases after the repetition of each operational cycle of the device, that is, by repeating the inductor (21) FIGS. 3a, or (21a) FIG. 3b, current feeding after each new charging of the energy reservoir-capacitor (7) FIGS. 2a, 2b. The end result in exhibit (24) FIGS. 4a, 4b is a function of the magnetic field's intensity and the device's operation time.

Concerning specific applications of this method for ion transport or chemical and nuclear reactions initiation, to which specific atoms nuclei or electrons react or are being transported, apart from inventor's previous invention 1001784/6/21995/OBI, no other method is known.

The present new method is important because it does not require intervention or entry into exhibit (24) FIGS. 4a, 4b, (e.g., using electrodes and/or chemical substances), and because the induced electrical tension is momentarily very powerful, because of the conductivity oscillations of the electronic switch arrangement (14) FIG. 2a or of the plasma switch (14) FIG. 2b, without the requirement for the initial power supply tension to be equally as big.

Like the inventor's previous invention #1001784/6/21995/OBI, the expected applications of the present invention are similarly extended to a great technological and scientific spectrum, where NMR and EPR, locomotion of charges, ions, nuclei and specific atoms in inaccessible regions is required, for illustration in Biology, Medicine, Chemical Industry, Nuclear Industry for selective energy supply to Chemical and Nuclear reactions, initiation at will of Chemical-Nuclear reactions, control of Chemical-Nuclear reactions, catalysis of chemical reactions for the supply of selected products between various other products, which cannot possibly be separated with other methods of energy supply, and the activation of exhibits with the Nuclear Magnetic Resonance (and/or Electron Paramagnetic Resonance) (26), (27), (28), FIG. 5 as it is employed today in the field of Diagnostics Medicine with great success and effectiveness, the Nuclear Magnetic Resonance phenomenon which is also based on the selective energy absorption by the atomic nuclei.

With this described method, electromagnetic radiation ($\sim 1/r^2$) is not produced to the greater percentage of the field's energy, because the intensity of the produced field weakens very fast ($\sim 1/r^3$) where r is the distance from the coil (21) FIGS. 4a, 4b.

The intensity of the field is that of a magnetic dipole, inversely proportional to the third power of the distance ($1/r^3$), a fact that indicates that the field's influence does not extend to a substantial distance and is not radiated according to $1/r^2$ law.

The produced field frequency can be outside the microwave band frequencies (being smaller), with good results.

Obviously, a variation of the proposed device-embodiment of the method described above, can also be materialized by, nevertheless, using a second auxiliary magnetic field to assist or to contribute together with the ambient Earth's magnetic field, in restoring the disturbed (under precession as described above) spins of nucleus and spins of electrons. Also, note, this second auxiliary field can used as substitute for the Earth's magnetic field, in part or in all, or this field can be used, being actually redundant, just for the shake of a novelty, with the device producing the same results as described above.

Appendix: Calculation of the Kervran-Pappas Nuclear Reaction Energy.

In order to calculate the energy exchange of the Kervran-Pappas reaction, the exact atomic masses for the related isotopes of Na, O, K from the "HANDBOOK of CHEMISTRY and PHYSICS" 82-nd Edition © 2001 by CRC Press LLC, Section 11, page-52, 59.) are employed.

The evolution of the Atomic Energy from the said reaction, is calculated by the formula:

$E = mc^2$

A) for Sodium atoms: $Na^{23}=22.989769700000$: 100% natural abundance, because there is only one isotope in nature.
B) for Oxygen atoms: Isotope $O^{16}=15.99491462200$ (99.757%), leading to $K^{39}=38.963706900000$—natural abundance: 93.2581%
Isotope $O^{17}=16.999131500000$ (0.038%), leading to $K^{40}=39.963998700000$—natural abundance: 0.0117%
Isotope $O^{18}=17.999160000000$ (0.205%), leading to $K^{41}=40.961826000000$—natural abundance: 6.7302%
Thus the mean mass for O=15.999404927439
C) for Potassium atoms:
K mean value from above=38.9637069×99.957+39.9639987×0.038+40.961826×0.205=38.968182
K books' mean value=39.098300000000
D): Mass changed unto Energy:
For $O^{16}$: DM=22.9897697+15.994914622−38.9637069=0.000020977422 Kgr/Mol (SI Units) 99.757%
For $O^{17}$: DM=22.9897697+16.9991315−38.969987=0.00002490125 Kgr/Mol (SI Units) 0.038%
For $O^{18}$: DM=22.9897697+17.99916−38.9681823=0.0000271037 Kgr/Mol (SI Units) 0.205%
Which, using $E=DMC^2$, C=299792458 m/s for the velocity of light, leads to exothermic (giving out energy) reactions for Na and all Isotopes of O, as follows:
E) Pappas' Exothermic Nuclear Reactions by Isotope:

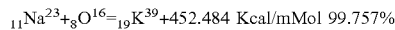

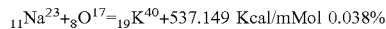

F) Conclusion: Mean energy released: $_{11}Na+_8O=_{19}K+$ 452.787 Kcal/mMol

SHORT DESCRIPTION OF THE DRAWINGS

FIG. 1:
The present block diagram shows the control unit (2) that includes a start-stop operation switch, timer and the rectification, electrical filtering and electrical current restriction unit (4), and its aim is to produce the flow of electrical energy from the main power supply to the switch circuitry arrangement and output coil-probe.

FIG. 2a:
The present drawing shows the basic probe input circuitry with electronic switch or other switch arrangement (14), which controls the discharge of the energy reservoir (7) stored in the inductor-probe (22).

FIG. 2b:
The present drawing shows an equivalent modification arrangement of another equivalent circuitry of 2a.

FIG. 3a:
The present drawing shows the inductor (22) which consists of the transport line (18) with its insulation (17) and the insulated ring (20) in which the inductive coil (21) which is comprised of one, two or few parallel conductors (21) that produce a variable intensity magnetic field is found.

FIG. 3b:
The present drawing shows the inductor (22) which consists of the transport power line (18) with its insulation (17) and the insulated ring (20) in which the inductive coil (21a) which is comprised of one, two or few twisted conductors (21a) that produce a variable intensity magnetic field is found.

FIG. 4a:
The present drawing shows the inductor (22), which consists of the transport power line (18) with its insulation (17) and the insulated ring (20) in which the inductive coil (21) which is comprised of one, two or few twisted (21a) or parallel (21) conductors is found, that produces a variable intensity magnetic field (23), in which biological material is exposed (24), that, in this particular case, is a human body.

FIG. 4b:
The present drawing shows the inductor (22) that consists of the transport power line (18) with its insulation (17) and the insulated ring (20) in which the inductive coil (21) which is comprised of one, two or few twisted (21a) or parallel conductors (21) that produces a variable intensity magnetic field (23), is found and in which any material (24) can be exposed. Also shown are nuclei or protons or electrons with a random spatial orientation, the magnetic spin vectors of the atomic nuclei (25) and/or electrons of exposed material (24) atoms (25).

FIG. 5:
Oscillogram of the NMR effect produced by an actual device, using only one induction magnetic field, and in the presence only of the magnetic field of the Earth, and embodying the presently described method.

The NMR sample response is portrayed as the "spike"—peak intense signal (26), (27), (28). "X" axis represents time domain. "Y" axis represents relative field amplitude. Notice: NMR traces are shown towards the end the of event. They are delayed some time after the main damped wave oscillating pulse first "hits" the sample and appear as an echo, as correctly expected by the known NMR relaxation.

The invention claimed is:
1. A method for multi-activation of ions and atoms with NMR and EPR, the method comprising:
providing an short-duration, high-current switch having a self induction of <10 μH;
coupling an inductor to the short-duration, high-current switch, the inductor further comprising a coil of a "few" conductors;
switching a high>10000 Amps current, with small<0.1 millisecond duration, through the inductor, in the presence of the Earth's magnetic field, so as to create a pulsed, damped wave, alternating magnetic field; and
applying the pulsating, damped wave, alternating magnetic field to a material so as to perturb the spin orientations of the nuclei /electrons of the material.
2. The method according to claim 1, wherein, the inductor further comprises a coil having one or two parallel conductors.
3. The method according to claim 1, wherein, the inductor further comprises a coil having one or two twisted conductors.
4. The method according to claim 1, wherein, the short-duration, high-current switch is selected from the group consisting of electronic switches, semiconductor switches, plasma switches, and spark gap switches.
5. A system for multi-activation of ions and atoms with NMR and EPR, the system comprising:
a power supply;
a capacitor reservoir coupled to the power supply;
a short-duration, high-current switch coupled to the capacitor reservoir, the switch being suitably activated or self-activated;
an inductor forming a coil comprised of a "few" conductors, a short-duration, high-current being generated through the inductor in the presence of the Earth's magnetic field; and wherein the inductor produces a damped wave alternating magnetic field suitable to perturb the spin orientations of nuclei /electrons of a material.

6. The system according to claim 5, wherein, the inductor further comprises a coil having one or two parallel conductors.

7. The system according to claim 5, wherein, the inductor further comprises a coil having one or two twisted conductors.

8. The system according to claim 5, wherein, the short-duration, high-current switch is selected from the group consisting of electronic switches, semiconductor switches, plasma switches, and spark gap switches.

9. The system according to claim 5, further comprising a second induction field contributing together with the ambient magnetic field of the Earth.

10. A method for multi-activation of ions and atoms with NMR and EPR, the method comprising:
coupling a capacitor reservoir to a power supply;
providing a short-duration, high-current switch coupled to the capacitor reservoir, the switch being suitably activated or self-activated and having a characteristic oscillation frequency;
forming an inductor coil;
generating a short-duration, high-current through the inductor at the switch's characteristic oscillation frequency and in the presence of the Earth's magnetic field; and
producing a damped wave, alternating magnetic field, having an intensity B in the inductor, suitable to perturb spin orientations of elementary atomic particles of a material.

11. The method according to claim 10, wherein the elementary atomic particles of a material are neutrons, protons and electrons, and wherein energy absorption by the elementary particles is greatest by those particles having a resonant frequency corresponding to $h\nu=\gamma Bh/2\pi$.

12. The method according to claim 10, wherein the magnetic field is applied into biological tissue so as to initiate biological nuclear transmutations through Nuclear Magnetic Resonance (NMR).

13. The method according to claim 10, wherein the magnetic field is applied into biological tissue so as to initiate catalysis of chemical reactions and the resulting chemical changes through Electron Paramagnetic Resonance (EPR).

14. The method according to claim 11, wherein the magnetic field is applied into biological tissue thereby causing ion formation in the biological tissue by energy absorption, and electrical current generation by movement of charged moieties across cellular membranes of said tissue.

* * * * *